United States Patent [19]

Hoefer

[11] 4,101,401

[45] Jul. 18, 1978

[54] FLUID ISOLATION ELECTROPHORESIS APPARATUS AND METHOD

[75] Inventor: Stanton A. Hoefer, San Francisco, Calif.

[73] Assignee: Hoefer Scientific Instruments, San Francisco, Calif.

[21] Appl. No.: 776,639

[22] Filed: Mar. 11, 1977

[51] Int. Cl.² .............................................. G01N 27/26
[52] U.S. Cl. .......................... 204/180 G; 204/299 R
[58] Field of Search ................. 204/180 G, 18 R, 299; 23/238 B

[56] References Cited

U.S. PATENT DOCUMENTS

| | | | |
|---|---|---|---|
| 3,129,158 | 4/1964 | Raymond et al. | 204/180 G |
| 3,506,554 | 4/1970 | Broome | 204/180 G |
| 3,563,880 | 2/1971 | Anderson | 204/299 |
| 3,719,580 | 3/1973 | Roberts et al. | 204/299 |
| 3,902,986 | 9/1975 | Nees | 204/299 |
| 3,932,265 | 1/1976 | Hoefer | 204/299 |
| 3,980,546 | 9/1976 | Caccavo | 204/299 |

*Primary Examiner*—Arthur C. Prescott
*Attorney, Agent, or Firm*—Flehr, Hohbach, Test, Albritton & Herbert

[57] ABSTRACT

Electrophoretic separation of samples in a running gel is obtained by depositing three layers of liquid in an outer container. The liquid layers have increasing specific gravities proceding from the uppermost to the lowermost layer. The upper and lower layers are electrically conductive buffer solutions which are immiscible with the center layer which is electrically insulating. A rack is provided for holding running gels in the outer container so that the upper end of the gels are in contact with the upper buffer layer and the lower end of the gels are in contact with the lower buffer layer. An upper and a lower electrode is provided in contact with each of the upper and lower buffer solutions respectively. A voltage impressed between the upper and lower electrodes provides a substantially unidirectional electrical field through the running gel and separation of samples in the running gel substantially free of distortion due to the absence of spurious electrical fields at the sides of the running gel adjacent to the central layer of electrically insulating fluid. Removal of the heat of electrophoresis and further reduction of distortion in separated samples is achieved by cooling the layered liquids using an immersed cooling coil or by recirculating the central layer through a heat exchanger.

16 Claims, 11 Drawing Figures

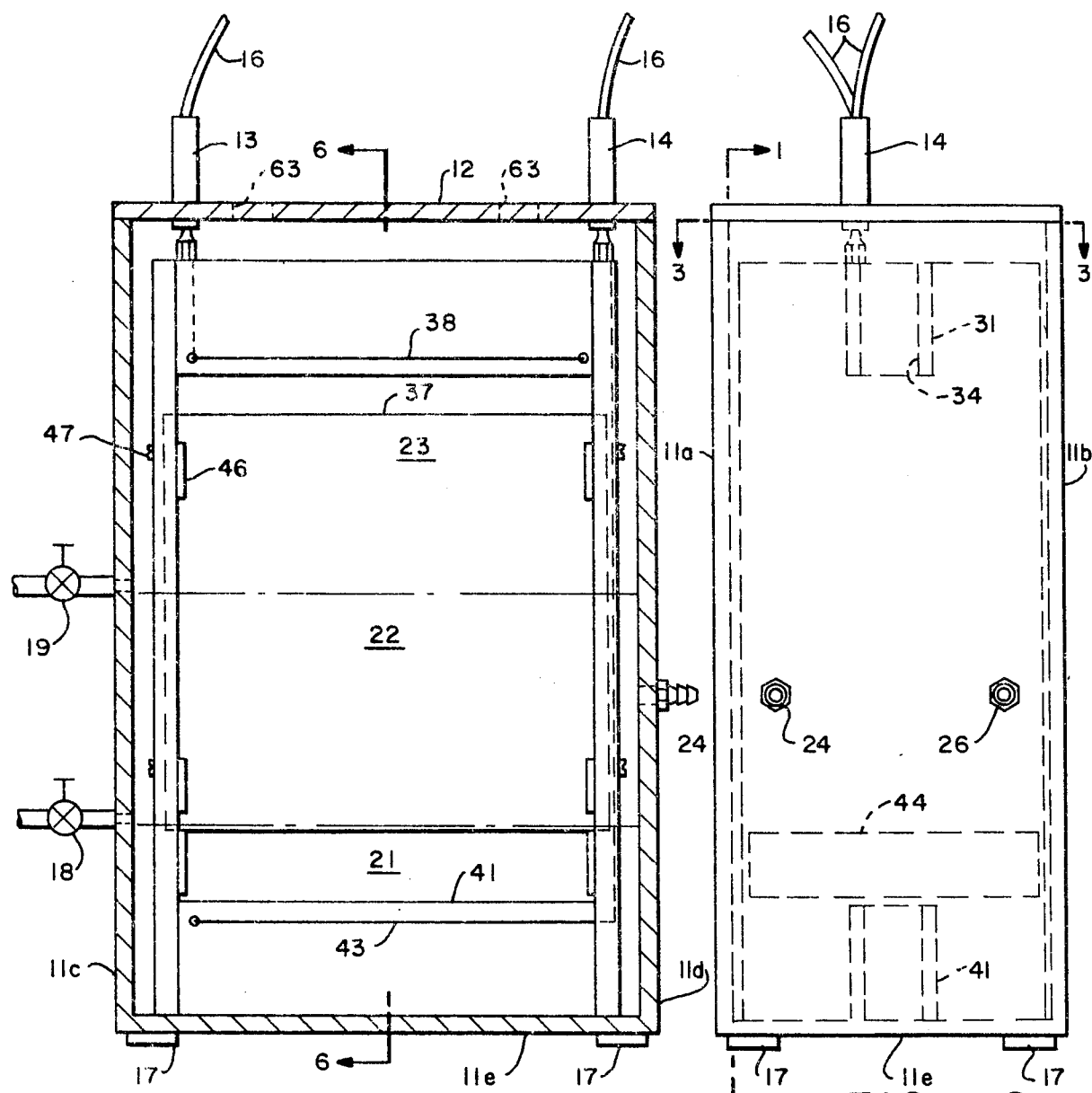
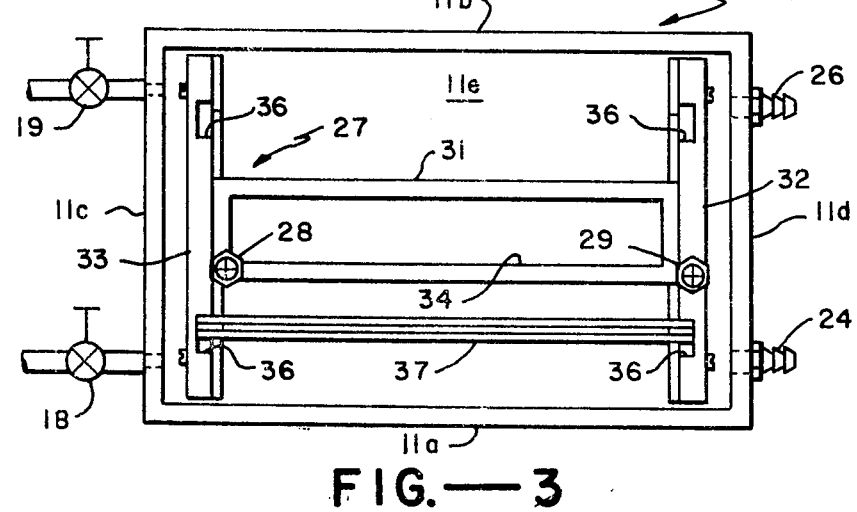

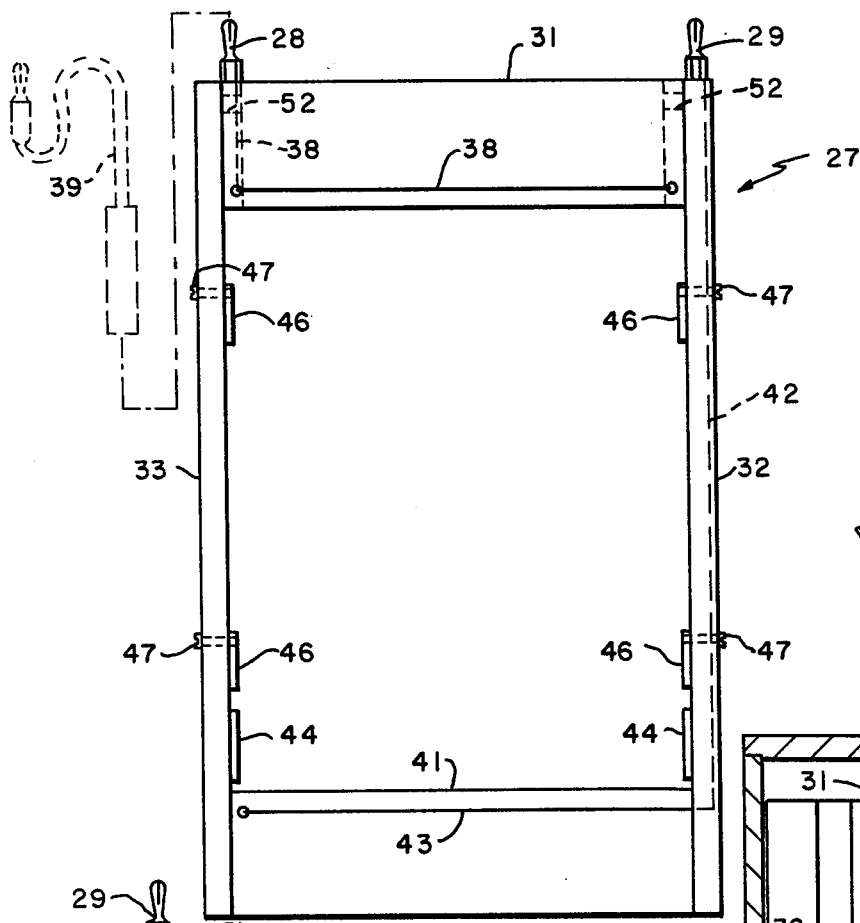
FIG.—4
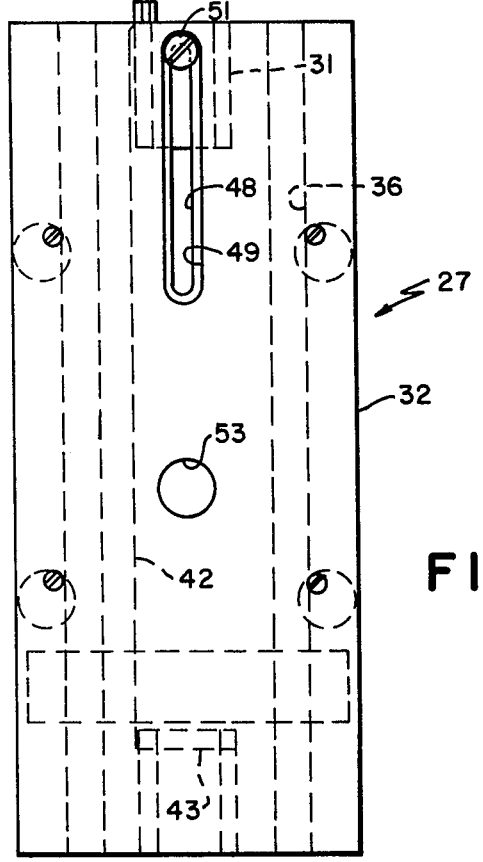
FIG.—5
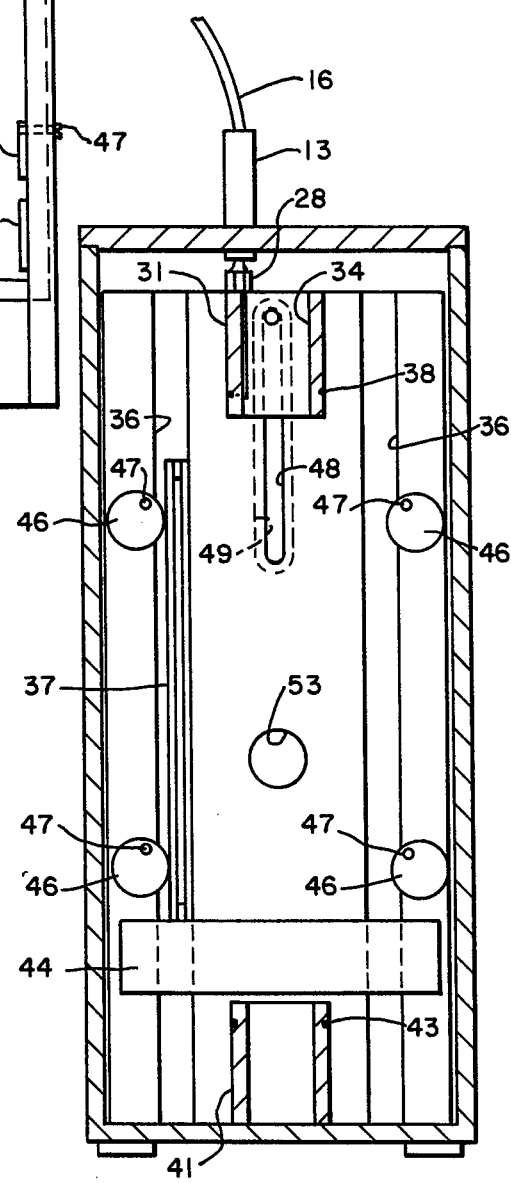
FIG.—6

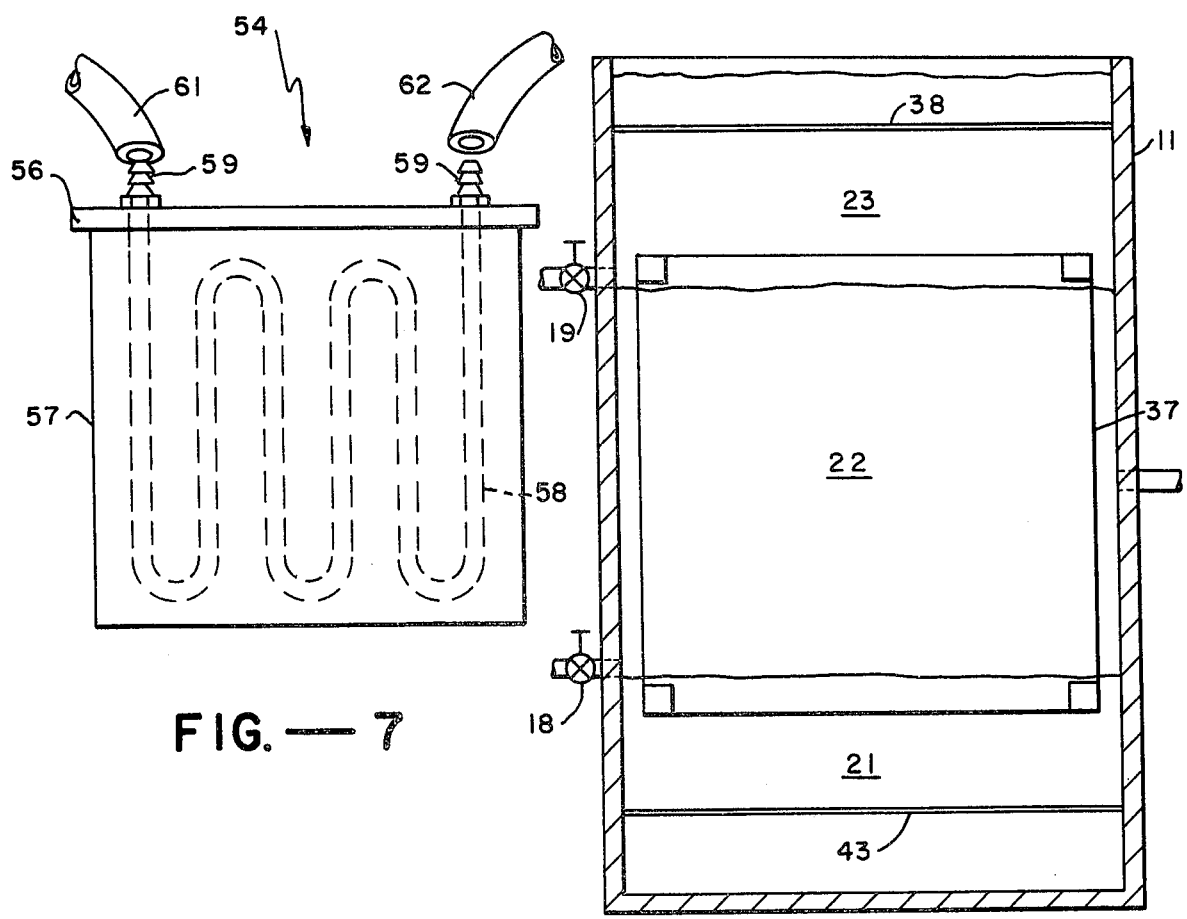
FIG.—7
FIG.—8
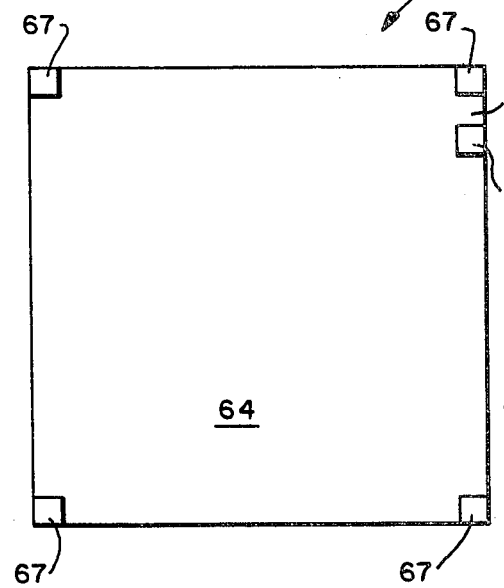
FIG.—9a
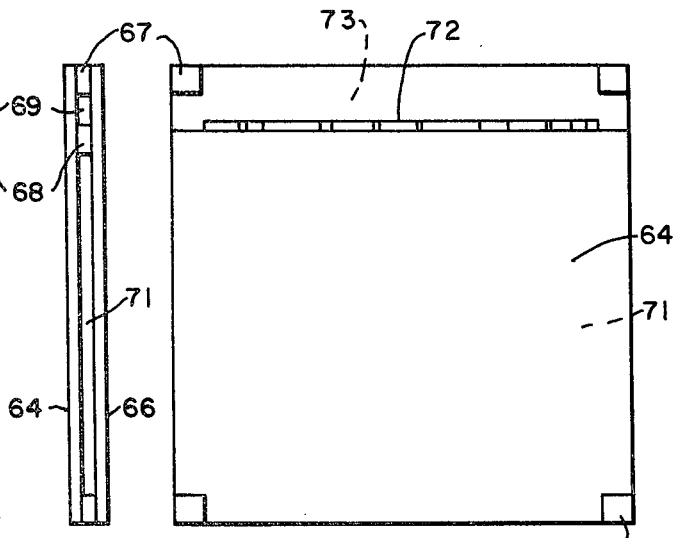
FIG.—9b  FIG.—10

FLUID ISOLATION ELECTROPHORESIS APPARATUS AND METHOD

BACKGROUND OF THE INVENTION

This invention relates to an electrophoresis device for separating samples in a running gel, and more particulary to such a device for use in separating samples in running gels of any geometric configuration in one or two dimensions.

In the past severe problems have been encountered obtaining leak-tight seals for performing gel electrophoresis between glass plates and within glass tubes. For example, vertical slab gel electrophoresis is accomplished by using two square glass plates separated along the two vertical edges by spacers to define the gel thickness, and thereafter sealing the two sides and the bottom of the space between the plates with a liquid-tight tape. Thereafter, the space between the plates is filled with acrylamide or agarose and then polymerized into a gel state. The result is a separating or "running" slab gel between the glass plates. The tape along the bottom of the pair of plates is removed to expose the bottom of the slab gel. The glass/gel sandwich is then inserted into either a rectangular grommet or some other type of compression seal so that the top protrudes through the grommet into a top compartment which is isolated from a bottom compartment by the grommet or compression seal. The lower end of the gel is exposed to the bottom compartment. Upper and lower electrically conductive buffer solutions are deposited in the top and bottom compartments respectively so that when a DC voltage is impressed between the upper and lower buffer solutions an electrical field is set up between the upper and lower exposed edges of the running gel. A sample deposited on the top of the running gel is caused to migrate through the gel by the electric field, certain components of the sample being stopped at certain stratum within the gel as the sample is seemingly "sieved" by the running gel as it migrates therethrough. A major drawback to this type of apparatus and method is that leakage between the glass plates and the rectangular grommet or compression seal is difficult to eliminate and can only be overcome absolutely by additional sealing with grease or other substances. Moreover, the sides of the running gel are exposed through leakage past the liquid tight tape to the upper and lower buffer solutions causing spurious electrical fields to be set up along the sides of the running gel. This results in distortion of the sample separation. Apparatus and methods are known for eliminating the rectangular sealing grommet, but such apparatus and methods do not remove the side leakage problem and the consequent sample separation distortion. Such apparatus and method are described in copending U.S. Application Ser. No. 569,838 in common ownership with the apparatus and method disclosed herein.

Tube gel electrophoresis is also practiced wherein the running gel is formed within a tube and thereafter disposed with the upper and lower ends of the running gel exposed to upper and lower buffer solutions similar to those described above for the slab gel electrophoresis devices. The sealing problem is retained in the known tube gel electrophoresis apparatus and methods. Seals between the gel holding tubes and the structure through which the tubes must pass are required. The structure serves to isolate electrically the upper and lower buffer solutions. Seal leakage is a problem as well as sample distortion due to overheating resulting from the electrical energy dissapated within the running gels during electrophoresis.

Two-dimensional electrophoresis involves running a sample in one direction through a running gel to obtain a separation of the sample into strata, and thereafter performing electrophoresis in a direction substantially orthogonal to the first separation direction to obtain a number of substrata in the sample. This achieves a finer component separation for the sample. In the past, when two-dimensional electrophoresis was performed using a tube shaped running gel, the first electrophoretic separation was completed and the tube gel was removed from the tube. A slab gel having the same thickness as the diameter of the tube gel was formed between glass plates as described above, the tube gel laid across the top of the slab gel, and the sample strata in the tube gel electrophoresed downward out of the tube gel into the slab gel to obtain substrata separation therein. When attempting two-dimensional electrophoresis in a slab gel, the side seals were removed after the first electrophoretic separation in one direction through the slab gel, and the previously open ends were thereafter sealed. The slab was placed in contact with the upper and lower buffer solutions at the newly exposed sides of the slab gel. Subsequent electrophoretic separation provided sample component substrata as described hereinbefore. However, the usual risk of sample distortion due to leakage and spurious electrical fields was compounded by the breaking and reforming of seals at the edges of the slab gel.

Consequently, a device and method are needed for performing either one or two dimensional electrophoresis wherein the sealing problem and distortion from spurious electric fields and lingering heat of electrophoresis is substantially reduced.

SUMMARY AND OBJECTS OF THE INVENTION

The apparatus disclosed herein provides for electrophoretic separation of samples within a running gel utilizing an outer container which forms an upper buffer space, an intermediate space adjacent to the upper buffer space, and a lower buffer space adjacent to the intermediate space. Adjacent spaces within the outer container are in communication. Structure is provided for holding the running gel in vertical orientation within the outer container so that the upper end of the gel extends into the upper space and the lower end of the gel extends into the lower space. An upper electrode is disposed in the upper space and a lower electrode is disposed in the lower space. Means is provided for removing the heat of electrophoresis from the intermediate space. The upper, intermediate and lower spaces are adapted to receive and hold upper buffer, electrically insulating and lower buffer solutions respectively having increasing relatives specific gravity in the order named. When a sample is placed on top of the running gel and an electrical potential is applied between the upper and lower electrodes, the upper and lower buffer solutions are electrically isolated, spurious electrical fields at the edges of the running gel adjacent to the electrically insulating fluid are prevented, seals are eliminated and the sample is separated within the running gel electrophoretically without distortion from overheating or spurious side electric fields.

The method includes stacking a sample to be separated atop a polymerized running gel and depositing a high specific gravity lower buffer solution inside a receiving chamber. An intermediate specific gravity electrically insulating solution which is immiscible with the lower buffer solution is laid over the lower buffer solution. Thereafter the method includes laying a low specific gravity upper buffer solution over the electrically insulating solution and immersing the running gel with the stacked sample in the layered solutions so that the lower end of the running gel enters the lower buffer solution and the upper end extends into the upper buffer solution. Upon impressing a voltage between the upper and lower buffer solutions the sample is separated in the running gel in the direction of the voltage gradient therein without distortion effects from spurious side electrical fields where the running gel is adjacent to the electrically insulating solution.

In general, it is an object of the present invention to provide an electrophoresis apparatus and method which greatly reduces the problems associated with leakage and sample separation distortion.

Another object of the present invention is to provide an electrophoresis apparatus and method which will perform either one or two dimensional electrophoresis without the necessity for breaking and remaking seals between first and second dimensional separations.

Another object of the present invention is to provide an electrophoresis apparatus and method with improved heat transfer characteristics and thereby reduced separated sample distortion due to overheating.

Another object of the present invention is to provide an improved electrophoresis apparatus and method which is simple to operate due to the removal of the requirement for obtaining high quality seals between adjacent solutions within the device.

Another object of the present invention is to provide an improved electrophoresis apparatus and method which may run samples through "naked" running gels, thereby obtaining superior cooling and allowing higher operating voltages, thereby producing faster sample separation in the running gels.

Additional objects and features of the invention will appear from the following description in which the preferred embodiment has been set forth in detail in conjunction with the accompanying drawings.

BRIEF DESCRIPTION OF THE DRAWINGS

FIG. 1 is a sectional side elevational view of the liquid isolation electrophoresis apparatus along the line 1—1 of FIG. 2.

FIG. 2 is an end elevational view of the fluid isolation electrophoresis device.

FIG. 3 is a plan view along the line 3—3 of FIG. 2.

FIG. 4 is a side elevational view of the rack contained in the liquid isolation electrophoresis device FIG. 5 is an end elevational view of the rack of FIG. 4.

FIG. 6 is a sectional view along the line 6—6 of FIG. 1.

FIG. 7 is a side elevational view of a cooling coil for use in the disclosed apparatus.

FIG. 8 is a diagram showing the operation of the apparatus of FIG. 1.

FIG. 9a is a front elevational view of a slab gel assembly for two-dimensional electrophoresis.

FIG. 9b is a side elevational view of the slab gel assembly of FIG. 9a.

FIG. 10 is a side elevational view of a slab gel assembly for two-dimensional electrophoresis using a tube gel.

DESCRIPTION OF THE PREFERRED EMBODIMENTS

FIG. 1 shows one embodiment of the liquid isolation electrophoresis device with the nearest side wall of an outer container 11 removed for clarity. Outer container 11 has two side walls 11a and 11b, two end walls 11c and 11d and a bottom wall 11e. Outer container 11 further has an opening in the top thereof which accepts a cover 12 formed to fit therein. Cover 12 has a pair of power sockets 13 and 14 mounted in fixed position therein. Electrical leads 16 are connected to power sockets 13 and 14 so that DC voltages may be connected thereto from a remote power source (not shown). Soft supporting feet 17 are provided at each corner of bottom wall 11e for supporting the liquid isolation electrophoresis apparatus on a laboratory bench top or counter.

A lower valve 18 is inserted through and fixed in wall 11c and an upper valve 19 is also inserted through and fixed in wall 11c. The interior of outer container 11 contains three separate spaces or volumes therein. A lower buffer space 21 is located at the bottom of outer container 11 co-terminous with bottom wall 11e. A central or intermediate volume or space 22 is located immediately above lower buffer space 21. An upper buffer volume space 23 is found within outer container 11 overlying central or intermediate space 22. Valve 18 passes through wall 11c just above the boundry between lower buffer space 21 and intermediate space 22. Upper buffer space 23 may occupy more or less of the space within outer container 11 above intermediate space 22 depending upon the vertical position of an upper buffer electrode to be hereinafter described. As shown in FIG. 1, upper buffer space 23 has a lower limit which is at the level of position in which valve 19 passes through wall 11c of container 11. Each of lower buffer, intermediate and upper buffer spaces 21, 22 and 23 respectively is in communication with the space adjacent thereto.

As seen in FIG. 2 a pair of hose fittings 24 and 26 pass through wall 11d, defining an inlet port and an outlet port respectively in communication with intermediate space 22. Couplings 24 and 26 thereby afford an inlet and outlet port for recirculation of liquid contained within intermediate space 22.

FIG. 3 shows cover 12 removed from container 11 so that an electrode and rack assembly 27 is visible in plan view. A pair of electrical terrminals 28 and 29 are shown attached to the upper edge of electrode/rack assembly 27 in position such that they mate with power sockets 13 and 14 in cover 12 respectively when cover 12 is placed on top of outer container 11.

FIG. 3 further shows a box-like connecting member 31 extending between opposite end plates 32 and 33 on the electrode/rack assembly 27. Box-like connecting member 31 extends between the upper edges of the end plates 32 and 33 having an opening 34 through the center thereof. End plates 32 and 33 have grooves 36 in the facing surfaces thereon which receive the edges of a slab gel assembly 37 to be hereinafter described in greater detail. FIG. 3 shows to pairs of facing grooves 36. It is envisioned that there may be any practical number of pairs of facing grooves 36 depending upon the number of slab gel assemblies in which it is desired to make simultaneous sample separations in the separation or running gel contained therein.

Power terminal 28 is mounted on the upper edge of box-like connecting member 31 having an electrode wire 38 connected thereto and extending along the length of box-like connecting member 31. In this fashion, electrode 38 extends across a major portion of upper buffer space 23. An extension conductor 39 is shown in ghost lines which connects power terminal 28 with power socket 13 in end cover 12 when box-like connecting member 31 is adjusted in vertical position by structure to be herein after described.

A lower box-like member 41 extends between the lower ends of end plate 32 and 33 having a shape substantially the same as box-like connecting member 31. Power terminal 29 is mounted atop end plate 32 having an electrical conductor 42 connected thereto extending vertically through end plate 32. Electrical conductor 42 may be an insulator conductor in which case it could be placed on the outer surface of end plate 32, or, as an alternative, situated in an open groove on the face thereof. Electrical conductor 42 is in turn connected to a lower electrode 43 extending across lower box-like connecting member 41. Lower electrode 43 is thereby situated within lower buffer space 21 in outer container 11 when electrode/rack assembly 27 is placed therein. A stop member 44 extends across the inwardly facing surfaces of end plates 32 and 33 serving to support slab gel assemblies 37 in grooves 36 at a predetermined height above the bottom of electrode/rack assembly 27 and therefore at a predetermined height above the inner surface of bottom wall 11e on outer container 11. Each groove 36 in end plates 32 and 33 has a pair of adjustable cams 46 associated therewith which operate to bear against the surfaces at the sides of slab gel assemblies 37 to thereby hold them firmly within grooves 36. Cams 46 are adjusted in position by loosening screws 47, positioning cams 46 in contact with the edge of slab gel assembly 37 and thereafter retightening screws 47.

FIG. 5 shows an elongate opening 48 formed near the upper end of plate 32. A similar elongate opening 48 is formed in a corresponding position on end plate 33. Both elongate openings 48 have a surrounding counter bore 49 which accepts the head of a screw 51 which extends through each elongate opening 48. A pair of threaded holes 52 located in opposite ends of box-like connecting member 31, as shown in FIG. 4, receive screws 51. It may be seen that box-like connecting member 31 is adjustable in height through a range limited by the length of elongate opening 48 when screws 51 are loosened. When the desired location in height for box-like member 31 is obtained, screws 51 are tightened so that the screw heads bear against the face of counter bore 49 to thereby fix box-like connecting member 31 in vertical position. Consequently, the distance between upper electrode 38 and lower electrode 43 is adjustable. This allows short separation or running gels in short slab gel assemblies 37 to be placed in grooves 36 and the central or intermediate space 22 to also be shortened so that the upper edge of short slab gel assembly 37 will extend into upper buffer space 23. As a result, the depth of a solution placed within upper buffer space 23 is lessened by lowering upper electrode 38 to a point where it is immersed in the fluid. Minimal head pressure is therefore exerted by solution in the upper buffer space 23 on the top of gels in slab gel assembly 37. In the event box-like connecting member 31 is lowered on electrode/rack assembly 27 by means of adjustment afforded by screws 51, extension connector 39 is utilized to provide power from power socket 13 immediately thereabove to power terminal 28 which is lowered with box-like connecting member 31.

FIG. 6 shows grooves 36 with stop member 44 extending thereacross so that slab gel assembly 37 is supported in grooves 36 at a predetermined height within outer container 11. Adjustable cams 46 are seen to rotate about an axis through the center of adjusting screws 47. As a result, adjustable cams 46 may be adjusted from a position completely overlying grooves 36 to a position wherein no part of adjustable cam 46 overlies groove 36. As shown in FIG. 6, when the edges of a slab gel assembly 37 are inserted into grooves 36, adjustable cams 46 may be turned about the axis of screws 47 to bear against one surface of slab gel assembly 37 near the edges thereof. Since there are two such adjustable cams 46 associated with each groove 36, two point contact against the surface of slab gel assembly 37 near each side of the assembly is obtained to thereby firmly hold slab gel assembly 37 between the adjustable cams 46 and one edge of groove 36. An opening 53 is formed in each of end plates 32 and 33 so that all portions of central or intermediate space 22 are interconnected, even when two slab gel assemblies 37 are placed within the two grooves 36 shown in this embodiment.

FIG. 7 shows a cooling coil assembly 54 which is formed to fit through opening 34 in box-like connecting member 31. An upper cooling coil plate 56 overlies a lower heat exchanger portion 57 having a serpentine passage 58 therethrough. The ends of serpentine passage 58 are terminated in fittings 59 which communicate serpentine passage 58 with inlet and outlet tube 61 and 62 respectively. Inlet and outlet tubes 61 and 62 are placed in sequence with a pump (not shown) and an external heat exchanger (not shown), so that a fluid pumped through serpentine passage 58 entering through tube 61 and exiting through tube 62 will carry away heat surrounding heat exchange portion 57 to be withdrawn from the fluid in the external heat exchanger prior to recirculation of the fluid through heat exchange portion 57.

Turning now to the operation of the fluid isolation electrophoresis apparatus, reference is made to FIG. 8 of the drawings which is in diagrammatic form, omitting some of the structural detail heretofore described. Outer container 11 is shown with an upwardly facing opening therein. Upper buffer space 23 is shown overlying central or intermediate space 22 within outer container 11. Intermediate space 22, in turn, is shown overlying lower buffer space 21 at the bottom of outer container 11. Upper electrode 38 is shown disposed in upper buffer space 23 and lower electrode 43 is shown disposed in lower buffer space 21. The three spaces 21, 22 and 23 are filled with liquids having different densities. The center phase or center liquid must be an inert non-polar liquid that provides electrical insulation. The center phase in intermediate space 22 therefore provides electrical isolation between upper buffer space 23 and lower buffer space 21. Further the center phase must not chemically react with any solution used in the upper or lower buffer spaces 23 and 21 respectively, or the separation gels contained within slab gel assembly 37 or any other separation gel holder utilized for electrophoretic sample separation. Another requirement of the center phase liquid is that it must not be miscible with any liquids used in upper and lower buffer spaces 23 and 21. It is convenient if the center phase liquid is of relatively low viscosity, and safety considerations require that it be non-toxic and have a high flash point. Acceptable center phase liquids now known are polybutene, polybutylene or polybutydiene, which each have a density which is less than one. The density of these liquids may be increased to a desired density, or specific gravity, of approximately 1.05 by adding a small amount of Freon 113 TM. These center phase liquids are preferred from a cost and cleanup standpoint, however, dibutylphthalate or one of the siloxanes (silicone oils) having a specific gravity of about 1.05 may be used, eliminating the need to adjust the density through the addition of Freon 113 TM. The dibutylphthalate has the disadvantage of attacking plexiglass, which would eliminate this convenient material for the structural parts of the apparatus. This is another reason for the preference for polybutene, polybutylene or polybutydiene mentioned above.

A liquid is first disposed in lower buffer space 21 which serves as a lower buffer solution. This solution contains buffer salts dissolved in water. Sufficient sucrose is dissolved in this lower buffer solution to make it attain a specific gravity which is greater than the center phase liquid and any solution placed within upper buffer volume 23. The addition of 24 percent sucrose solution brings the density of the lower buffer solution within lower buffer space 21 to about 1.10. Subsequently, the center phase liquid having a specific gravity of about 1.05 is laid atop the lower buffer solution, in effect floating thereon. An upper buffer solution is then deposited within upper buffer space 23 having a density near 1.0. The upper buffer solution therefore floats atop the center phase liquid within intermediate space 22. Means for holding a running gel in slab gel form, which means is disclosed herein as electrode/rack assembly 27 and slab gel assembly 37 are used to immerse the separation or running gel in the layered three phases of liquid within outer container 11. The upper edge of slab gel assembly 37 extends into upper buffer space 23, therefore being in contact with the upper buffer solution contained therein. The lower edge of the running gel contained within slab gel assembly 37 is shown extending into lower buffer space 21, therefore being in contact with the lower buffer solution contained therein. The side of slab gel assembly 37 need not necessarily be sealed, since the center phase liquid is electrically insulating and there can be no appreciable conduction between the sides of a running gel adjacent to the center phase liquid and the center phase liquid itelf. Therefore, spurious electrical fields at the sides of the running gel within slab gel assembly 37 are absent, and the electrical field influencing the running gel established when DC voltage is applied to upper and lower electrodes 38 and 43 respectively, is substantially unidirectional between the upper and lower buffer solutions. Sample separation occuring due to the sieving effect of the running gel as the sample is urged therethrough under the influence of the electric field is substantially free of distortion because of the unidirectional electrical field characteristic obtained by eliminating the spurious side electrical fields. Running gels may even be "naked" within the center phase liquid in intermediate space 23, which allows for greater cooling capability as heat of electrophoresis is more easily removed from the "naked" running gel. It is required in such a case that an upper pair of surrounding strips or plates be used at the upper end of the running gel for purposes of stacking and retaining samples on top of the running gel.

Note that in FIG. 8, valve 18 is located at the interface of the lower buffer solution in lower buffer space 21 and the center phase liquid in intermediate space 22. This allows the center phase liquid to be drawn off from outer container 11 when it is necessary to empty the container. It would also be possible to utilize lower valve 18 to place the center phase liquid within outer container 11 after the higher density lower buffer solution had been deposited in the bottom of outer container 11 up to the level of lower valve 18. Upper valve 19 is shown at the interface of the upper buffer solution and the center phase liquid in upper buffer space 23 and intermediate space 22 respectively. Opening of upper valve 19 allows upper buffer solution to be drawn off when outer container 11 is to be emptied. The positioning of upper valve 19 is of lesser importance, however, since upper buffer solution is less expensive than the center phase liquid and efforts to conserve upper buffer solution are not as necessary as efforts to conserve center phase liquid. Consequently, as seen in FIG. 1 of the drawings, upper valve 19 is located in a lower position in wall 11c of outer container 11 to accommodate the vertical adjustment of upper electrode 38 within upper buffer space 23. Upper buffer solution may still be drawn off through upper valve 19 when center phase liquid is deposited within outer container 11 to a level above upper valve 19, by drawing off sufficient center phase liquid through lower valve 18 until the interface between upper buffer solution and center phase liquid is lowered to the upper valve 19 level. Thereafter, upper buffer solution is drawn off through valve 19, and when it is substantially all removed from container 11 the remainder of center phase liquid is thereafter drawn off through lower valve 18.

Cooling of the separation or running gels during electrophoresis is necessary so that the process may be carried on at an acceptable rate. The greater the cooling efficiency of the device, the higher the rate of separation, and the less time involved in obtaining gels with separated samples therein. As mentioned above, naked gels may be supported within the disclosed apparatus so that the gels conduct heat directly to the center phase liquid. When insulating plates are used, as shown in slab gel assembly 37, which surround the separating gels, the heat of electrophoresis must pass through the insulating plate to the center phase liquid. In any event, heat of electrophoresis collected by the center phase liquid within intermediate space 22 must thereafter be removed from outer container 11 or distortion of the sample separation within the gels will result. The cooling coil assembly 54, FIG. 7, in one method of cooling, is placed within opening 34 in box-like connecting member 31 and supported therein by the flange formed by top plate 56 overlying heat exchange portion 57. A pair of holes 63 are formed in cover 12 which allow passage of inlet and outlet tubes 61 and 62 therethrough so that the liquid circulated through serpentine passage 58 may carry the heat transferred to the circulating liquid from the center liquid phase to the external heat exchanger. Thereafter the circulating liquid in colled condition is redirected to serpentine passage 58 through inlet tube 61 to collect and remove additional heat from center phase liquid within intermediate space 22. In this fashion all three layers of liquid within outer container 11 are held at or near 0° C. for good heat conduction and thus higher voltage gradients within the separating gels. The separating or running gels as mentioned above, may be run "naked" for superior heat dissipation therefrom, without spurious electrical field effects along the length of the gel.

An alternative method of cooling separating or running gels in the disclosed apparatus involves pumping the center liquid phase within intermediate space 22 out of outer container 11 through outlet port 26 and directing it to an external heat exchanger (not shown) for removing the heat of electrophoresis therefrom. The cooled center phase liquid is thereafter redirected to intermediate space 22 through inlet port 24 to absorb more heat from the running gel, thereby reducing the probability of separated sample distortion within the gels. The center phase liquid being immiscible with the upper and lower buffer solutions, and being greater in density than the upper buffer solution and lower in density than the lower buffer solution, retains its position therebetween in spite of the moderate amounts of turbulence induced within the center phase liquid by the recirculation through inlet and outlet ports 24 and 26 respectively.

The apparatus disclosed herein is capable of additionally performing what is termed two-dimensional electrophoresis in which both dimensions of separation of a sample within a separating gel may be accomplished in the slab gel without any disassembly and reassembly steps associated with slab gel assembly 37. Referring to FIGS. 9a and 9b, a slab gel assembly 37 is shown having a front insulating plate 64 and a rear insulating plate 66. Spacers 67 are located at the four corners of the front and rear insulating plates 64 and 66 for the purpose of separating the insulating plates to form a space therebetween. The two sides and bottom of the space between plates 64 and 66 in FIG. 9a are sealed with a tape, and a gel solution in liquid form is poured within the space. The gel solution is polymerized to a gel-like. The assembly of FIGS. 9a and 9b further includes an additional spacer 68 located a predetermined distance down one side of the slab gel assembly 37 to form an opening 69 between one of the corner spacers 67 and the additional spacer 68. Usually a stacking gel layer is then poured above the polymerized running gel at a level such that it spans opening 69. The stacking gel is also polymerized to a gel like state. While the remainder of the process weill be described in terms of a composite gel — stacking gel, it is also possible to utilize only a running gel between plates 64 and 66 with a small amount of stacking gel in opening 69 upon which a sample will thereafter be laid. The tape may be removed from the two sides and the bottom of slab gel assembly 37 at this point, so that all four edges of a composite slab gel 71 sandwiched between front and rear insulating plates 64 and 66 are now exposed at the edges of slab gel assembly 37. It may be desirable, however, to only remove a segment of the side tape overlying opening 69 and a corresponding segment of tape on the side opposite opening 69. In any event it is necessary to expose the two sides of the layer of polymerized stacking gel at least. It may also be desirable, though not an absolute requirement, to seal the top space between plates 64 and 66. The primary reason for the alternative of leaving most of the tape on the edges of slab gel assembly 37 and adding it to the top edge, is to provide an easy means of retaining the plates 64 and 66 together in assembly 37.

Slab gel assembly 37 of FIGS. 9a and 9b is then placed within electrodes/rack assembly 27 with opening 69 extending upwardly. A sample is placed atop the stacking gel in opening 69, and electrophoretic separation of the sample is performed within the stacking gel layer aligned with opening 69 and extending between upper and lower buffer spaces 23 and 21 respectively. Subsequently, slab gel assembly 37 is removed from electrode/rack assembly 27, and rotated through 90° so that the separated sample extends through the stacking gel layer along the upper edge of slab gel 71. Slab gel assembly 37 is then re-inserted in electrode/rack assembly 27 in the 90° orientation, and electrophoresis is once again performed. As a consequence, the strata of separated sample obtained in the first seperation of the sample in the stacking gel with opening 69 extending upwardly, are further separated into substrata within slab gel 71 due to the second electrophoretic separation. In summary, a first sample separation is performed at one edge of composite slab gel 71, followed by a second separation of the sample components in a direction substantially orthogonal to the direction of the first separation. The sample is thereby separated into fine component parts due to the two-dimensional electrophoresis without disturbing slab gel 71 within slab gel assembly 37.

Two-dimensional electrophoresis may also be performed utilizing a sample initially separated in a tube gel. FIG. 10 shows a tube gel 72 within which a sample has been initially separated. Tube gel 72 is laid atop a polymerized separation gel 71 contained between front and rear insulating plates 64 and 66 as in FIG. 9 above. Tube gel 72 is normally surrounded by a stacking gel 73, as in any sample prior to electrophoretic separation within a separating gel. The thickness of slab gel 71 in FIG. 10 is fixed by corner spacers 67 to be approximately the same as the diameter of the tube gel 72. The assembly of FIG. 10 is thereafter placed within grooves 36 in electrode/rack assembly 27 inside outer container 11 having upper buffer solution, central liquid phase and lower buffer solution in spaces 23, 22 and 21 respectively of increasing specific gravity in the order named. As a result, the strata of separated sample within tube gel 72 are further separated into subtrata within separating gel 71 in a vertical direction as seen in FIG. 10.

The disclosed method for separating a sample electrophoretically in a separation or running gel assembly within an electrophoresis chamber includes the step of depositing a high specific gravity lower buffer solution in the bottom of the chamber upon which is laid an intermediate specific gravity electrically insulating solution which is immiscible with the lower buffer solution. Thereafter, a low specific gravity upper buffer solution is laid over the electrically insulating solution, and the running gel assembly including the sample is immersed into the layered solutions and positioned therein so that the lower end of the running gel is in contact with the lower buffer solution and the upper end of the running gel assembly is in contact with the upper buffer solution. The step of impressing a voltage between the upper and lower buffer solutions causes electrophoretic separation of the sample in the running gel assembly in the direction of the voltage gradient therein without distortion effects from spurious electrical fields at the sides of the running gel assembly which are adjacent the electrically insulating solution. The method also includes the step of cooling the electrically insulating solution so that the heat generated by electrophoresis is transferred from the electrophoresis chamber and separated sample distortion is diminished. The cooling step is performed either by exchanging heat within the electrophoresis chamber with a circulating fluid externally, or by recirculating the electrically insulating solution located between the upper and lower buffer solutions and removing the heat of electrophoresis collected thereby externally of the electrophoresis chamber during the circulation. The method disclosed herein further includes the process step of repositioning the running gel after an initial sample separation by electrophoresis so that it is oriented orthogonally to the original position within the electrophoresis chamber. In this fashion, separation strata from the sample during the first electrophoresis operation are further separated into substrata during the second electrophoresis operation. A two-dimensional separation of a sample within a running gel is thereby achieved without disassembly and reassembly steps associated with the running gel assembly and absent any sample separation distortion due to spurious side fields at the edges of the separation gel.

An apparatus and method have been diclosed herein which provide for fast electrophoretic separation of samples within a running gel, reduced distortion in separated samples normally seen in prior art apparatus and methods due to leakage between upper and lower buffer solutions and leakage between the buffer solutions and the running gels resulting in spurious electrical fields at the edges of the running gels, as well as reduced distortion caused by high localized heating due to the electrical energy dissipation within the running gels.

What is claimed is:

1. Apparatus for electrophoretic separation of samples within a running gel, comprising an outer container forming therein an upper buffer space, an intermediate space adjacent to said upper buffer space and a lower buffer space adjacent to said intermediate space, each of said spaces being in fluid communication with the adjacent space, means for holding the running gel in vertical disposition within said outer container so that the running gel extends from said upper buffer, through said intermediate, to said lower buffer spaces, an upper electrode disposed in said upper buffer space, a lower electrode disposed in said lower buffer space, and means for removing heat energy from said intermediate space, whereby a sample placed atop the running gel is separated electrophorectially therein when an electrical potential is applied between said upper and lower electrodes, and said upper buffer, intermediate, and lower buffer spaces are filled with upper buffer, electrically insulating, and lower buffer solutions respectively having increasing relative specific gravity in the order named.

2. Apparatus as in claim 1 together with means for adjusting the vertical distance beween said upper and lower electrodes, whereby said upper and lower electrodes are maintained in said upper and lower buffer spaces respectively while accommodating differing lengths of running gels extending therebetween.

3. Apparatus as in claim 1 wherein said means for removing heat energy comprises an inlet port and an outlet port through said outer container walls in communication with said intermediate space, said outlet port being adapted to be coupled to a pump and said inlet port being adapted to be coupled to a heat exchanger, whereby the electrically insulating solution in said intermediate space is circulated through said inlet and outlet ports to remove the heat of electrophoresis therefrom.

4. Apparatus as in claim 1 wherein said means for removing heat energy comprises a cooling coil formed to fit within said outer container, an inlet end and an outlet end on said cooling coil, an inlet tube and an outlet tube connected to said inlet end and outlet end respectively, said inlet and outlet tubes exiting said outer container and being adapted to couple with a heat exchanger and a pump respectively, whereby the heat of electrophoresis is removed when a circulating fluid flows in said cooling coil.

5. Apparatus as in claim 1 wherein the running gel is retained between electrically insulating plates, and wherein said means for holding comprises a rack supported within said outer container receiving and retaining the electrically insulating plates so that the upper edges thereof extend into said upper buffer space and the lower edges thereof extend into the lower buffer space.

6. Apparatus as in claim 1 wherein the running gel is retained in a tube, and wherein said means for holding comprises a clamp engaging the tube in fixed position so that the upper end thereof extends into said upper buffer space and the lower end thereof extends into the lower buffer space.

7. Apparatus as in claim 1 together with upper and lower electrode terminals connected to said upper and lower electrodes respectively, a cover for said outer container, and mating power connectors for said upper and lower electrode terminals respectively being fixed in said cover, whereby power is removed from said upper and lower electrodes when said cover is removed.

8. Apparatus as in claim 1 together with a valve disposed in said outer container wall in communication with said intermediate space, whereby electrically insulating solution is drawn out of said outer container when said valve is opened.

9. Apparatus as in claim 1 together with a first valve disposed in said outer container wall in communication with said upper buffer space and a second valve disposed in said outer container wall in communication with said intermediate space, whereby upper buffer solution and electrically insulating solution are drawn out of said outer container when said first and second valves are opened respectively.

10. Apparatus for electrophoretic separation of a sample within a running slab gel comprising an outer container forming therein an upper buffer space, a lower buffer space and an intermediate space therebetween, adjacent ones of said upper buffer intermediate and lower buffer spaces being in communication one with the other, a rack configured to fit within said outer container extending from said upper buffer space to said lower buffer space, means for retaining the running slab gel in said rack so that the upper and lower ends thereof enter said upper and lower buffer spaces respectively, means for applying an electrical potential between said upper and lower buffer spaces, means for cooling said intermediate space, so that when said upper buffer, intermediate, and lower buffer spaces are filled with upper buffer solution, electrically insulating solution immiscible with buffer solution, and lower buffer solution respectively having increasing relative specific gravity in the order named, spurious electrical fields at the sides of the slab gel within the electrically insulating solution are avoided.

11. Apparatus as in claim 10 together with opposing square insulating plates retaining said slab gel therebetween, and means for securing said square insulating plates in spaced relation, so that when the sample is separated into strata within the slab gel in one direction, and said opposing square plates are turned to a position substantially orthogonal to the initial position in said means for retaining, the strata are separated into substrata in a direction substantially orthogonal to said one direction.

12. A method for electrophoretically separating a sample in a running gel assembly within an electrophoresis chamber, comprising the steps of depositing a high specific gravity lower buffer solution in the chamber, laying an intermediate specific gravity electrically insulating solution immiscible with the lower buffer solution over the lower buffer solution, laying a low specific gravity upper buffer solution over the electrically insulating solution, immersing the running el assembly in the layered solutions positioned so that the lower end of the assembly enters the lower buffer solution, and impressing a voltage between the upper and lower buffer solutions, whereby the sample is separated in the running gel in the direction of the voltage gradient therein without distorting effect from spurious electrical fields at the side of the running gel adjacent the electrically insulating solution.

13. The method of claim 12 together with the step of recirculating the electrically insulating solution, whereby heat generated by electrophoresis is transported from the electrophoresis chamber and sample separation distortion is diminished.

14. The method of claim 12 together with the step of repositioning the running gel assembly so that it is oriented substantially orthogonal to the original immersing position, whereby a two-dimensional separation of the sample in the running gel is achieved.

15. A fluid isolation electrophoresis apparatus, comprising an outer container, a lower buffer solution having a high density in the bottom of said container, an electrical insulation solution being immiscible with said lower buffer solution and having an intermediate density laid atop said lower buffer solution, an upper buffer solution being immiscible with said electrical insulation solution and having a low density laid atop said electrical insulation solution, means for holding a separating gel within said outer container so that the separation gel extends through said electrical insulation solution with the gel upper end in said upper buffer solution and the gel lower end in said lower buffer solution, a lower electrode in contact with said lower buffer solution, an upper electrode in contact with said upper buffer solution, whereby a sample placed on the separating gel is separated therein by a voltage gradient of substantially uniform direction when a voltage is impressed across said upper and lower electrodes, and means for removing the heat of electrophoresis from said electrical insulation solution.

16. An electrophoresis apparatus as in claim 15 wherein said means for holding includes a pair of substantially flat insulating plates and the separating gel is a slab gel retained therebetween, whereby two-dimensional electrophoretic separation of the sample is obtained when said voltage gradient of substantially uniform direction is impressed upon the separation gel in orthogonal directions in sequence.

* * * * *